US009556483B2

(12) United States Patent
Lee et al.

(10) Patent No.: US 9,556,483 B2
(45) Date of Patent: Jan. 31, 2017

(54) METHODS OF SCREENING FOR BINDING INTERACTION USING SETS OF MICROPARTICLES AND UNIQUE PROBES

(71) Applicant: ONE LAMBDA, Canoga Park, CA (US)

(72) Inventors: Jar-How Lee, Los Angelos, CA (US); Terrence Chen, West Hills, CA (US); Thoa Nong, Alhambra, CA (US)

(73) Assignee: ONE LAMBDA, INC.

( * ) Notice: Subject to any disclaimer, the term of this patent is extended or adjusted under 35 U.S.C. 154(b) by 0 days.

(21) Appl. No.: 14/293,609

(22) Filed: Jun. 2, 2014

(65) Prior Publication Data

US 2014/0272976 A1 Sep. 18, 2014

Related U.S. Application Data

(62) Division of application No. 12/114,430, filed on May 2, 2008, now Pat. No. 8,748,090.

(60) Provisional application No. 60/915,920, filed on May 3, 2007.

(51) Int. Cl.

| | |
|---|---|
| ***G01N 31/22*** | (2006.01) |
| ***G01N 33/52*** | (2006.01) |
| ***C12Q 1/68*** | (2006.01) |
| ***C40B 30/04*** | (2006.01) |
| ***C07H 21/02*** | (2006.01) |
| ***C07H 21/04*** | (2006.01) |
| ***G01N 33/569*** | (2006.01) |
| ***G01N 33/68*** | (2006.01) |

(52) U.S. Cl.

CPC ........... *C12Q 1/6881* (2013.01); *C12Q 1/6816* (2013.01); *G01N 33/56977* (2013.01); *G01N 33/6845* (2013.01)

(58) Field of Classification Search

CPC ....... C12Q 1/68; C12Q 1/6816; C12Q 1/6881; G01N 33/6845; G01N 33/56977

USPC .......... 422/430; 435/6.1, 91.2, 287.2; 506/9; 536/23.1, 24.3

See application file for complete search history.

(56) References Cited

U.S. PATENT DOCUMENTS

| | | | |
|---|---|---|---|
| 5,595,890 A | 1/1997 | Newton et al. | |
| 6,125,194 A | 9/2000 | Yeh et al. | |
| 6,207,379 B1 | 3/2001 | Lee et al. | |
| 6,449,562 B1 | 9/2002 | Chandler et al. | |
| 6,514,714 B1 | 2/2003 | Lee et al. | |
| 6,551,784 B2 | 4/2003 | Fodor et al. | |
| 2002/0155618 A1* | 10/2002 | O' Hagan | 436/172 |
| 2003/0165865 A1 | 9/2003 | Hinkel et al. | |
| 2003/0165925 A1 | 9/2003 | Saito et al. | |
| 2006/0008826 A1* | 1/2006 | Liu | 435/6 |
| 2006/0204071 A1 | 9/2006 | Ortyn et al. | |
| 2006/0292601 A1 | 12/2006 | Tam | |
| 2007/0037195 A1 | 2/2007 | Ho | |
| 2007/0238140 A1* | 10/2007 | Pentoney et al. | 435/7.92 |

FOREIGN PATENT DOCUMENTS

| | | | |
|---|---|---|---|
| AU | WO2006/060872 | * | 6/2006 |
| JP | 2004/529618 | | 9/2004 |

OTHER PUBLICATIONS

Hurley et al, A simple, bead-based approach for multi-SNP molecular haplotyping, 2004, Nucleic Acids Research, 32, e186, pp. 1-7.*
Hurley et al, A simple, bead-based approach for multi-SNP molecular haplotyping, 2004, Nucleic Acids Research, 32, e186, pp. 1-7, Supplementary information, pp. 1-4.*
Bodmer et al., Nomenclature for factors of the HLA system, 1998. *Hum. Immunol.* 60: 361-78 (1999) Part 1.
Bodmer et al., Nomenclature for factors of the HLA system, 1998. *Hum. Immunol.* 60: 379-95 (1999) Part 2.
Bugawan et al., A method for typing polymorphism at the HLA-A locus using PCR amplification and immobilized oligonucleotide probes. *Tissue Antigens*. 44: 137-47 (1994).
Colinas et al., Multiplexed genotyping of beta-globin variants from PCR-amplified newborn blood spot DNA by hybridization with allele-specific oligodeoxynucleotides coupled to an array of fluorescent microspheres. *Clin. Chem*. 46: 996-8 (2000).
Drago et al., Genotyping of the Kidd blood group with allele-specific oligodeoxynucleotides coupled to fluorescent microspheres. *Transfus. Med.* 15(6): 499-501 (2005).
European Search Report, EP 08 74 7325, dated Jun. 15, 2010.
International Search Report, United States Patent and Trademark Office, PCT/US2008/62194 dated Jul. 28, 2008.
Itoh et al., Four-digit allele genotyping of the HLA-A and HLA-B genes in Japanese patients with Behcet's disease by a PCR-SSOP-Luminex method. *Tissue Antigens*, 67(5): 309-4 (2006).
Marsh et al., Nomenclature for factors of the HLA system, 2000. *Hum. Immunol.* 62: 419-44 (2001) Part 1.
Marsh et al., Nomenclature for factors of the HLA system, 2000. *Hum. Immunol.* 62: 445-68 (2001) Part 2.
Martins et al., The application of true internal controls to multiplexed fluorescent immunoassays. *J. Clin. Ligand Assay*, 26(2): 93-7 (2003).
Ng et al., Large-scale oligonucleotide typing for HLA-DRB1/3/4 and HLA-DQB1 is highly accurate, specific, and reliable. Tissue Antigens. 42: 473-9 (1993).
Pei et al., Flow cytometric detection of HLA antibodies using a spectrum of microbeads, *Hum. Immunol.* 60(12): 1293-302 (1999).

(Continued)

*Primary Examiner* — Narayan Bhat

(74) *Attorney, Agent, or Firm* — Marshall Gerstein & Borun LLP

(57) ABSTRACT

The present invention relates to a kit for conducting a method of measuring binding interactions using multiple sets of microparticles, wherein said set has the same identifiable characteristic and wherein one of more sets comprise subsets of microparticles and said subset presents at least one unique probe that acts as a binding partner for a target molecule in a biological sample. In particular, the invention provides for a kit for conducting a method of DNA-based tissue-typing antigens in donor tissue or recipient tissue using these multiple sets of microparticles.

11 Claims, No Drawings

(56) References Cited

OTHER PUBLICATIONS

Rahal et al., DNA typing by microbead arrays and PCR-SSP: Apparent false-negative or positive hybridization or amplification signals disclose new HLA-B and -DRB1 alleles, *Tissue Antigens*, 71(3): 238-41 (2008).

Salter et al., Mutually exclusive public epitopes for HLA-A,B,C molecules. *Hum. Immunol*. 26: 85-9 (1989).

Terasaki et al., Microdroplet testing for HLA-A, -B, -C and -D antigens. *Am. J. Clin. Pathol* 69: 103-20 (1978).

Waterboer et al., Suppression of non-specific binding in serological Luminex assays. *J. Immunol. Meth*. 309(1-2): 200-4 (2006).

Written Opinion in corresponding PCT/US08/62194 dated Jul. 28, 2008.

Xu et al., Multiplexed SNP genotyping using the Qbead system: A quantum dot-encoded microsphere-based assay. *Nucl. Acids Res*. 31(8): E43 (2003).

* cited by examiner

METHODS OF SCREENING FOR BINDING INTERACTION USING SETS OF MICROPARTICLES AND UNIQUE PROBES

This application is a divisional application of U.S. patent application Ser. No. 12/114,430 filed May 2, 2008, which claims priority to U.S. Provisional Patent Application No. 60/915,920, filed May 3, 2007, which are incorporated by reference herein in their entirety.

FIELD OF INVENTION

The present invention relates to methods for screening for binding interactions using multiple sets of microparticles, wherein said set has the same identifiable characteristic and wherein one of more sets comprise subsets of microparticles and said subset presents at least one unique probe that acts as a binding partner for a target molecule in a biological sample. In particular, the invention provides for methods of detecting tissue-typing antigens in donor tissue or recipient tissue using these multiple sets of microparticles.

BACKGROUND

One such tissue-typing antigen is human leukocyte antigen (HLA). Individuals may be sensitized to HLA antigens during pregnancy, or by blood transfusion or previous organ grafts. Testing to determine sensitivity to HLA alleles is relevant to tissue and organ transplantation where the presence in the recipient of antibodies against HLA antigens of the donor (donor specific crossmatch) is predictive of a high risk of graft rejection. It is a standard practice in the transplant field to test all potential recipients against a panel of HLA antigens selected to represent a human population and the percentage of HLA alleles against which the serum is reactive is determined. In this panel reactive antibody (PRA) testing reaction of a patient's serum against a high percentage of HLA alleles present in a normal human population is predictive of a high risk of graft rejection.

The HLA locus is highly polymorphic in nature. As disclosed in the Nomenclature for Factors of the HLA System 2000 (Hum. Immunol.; 62(4):419-68), 2001) there are 124 HLA-A alleles, 258 HLA-B alleles, 74 HLA-C alleles, 221 HLA-DRB1 alleles, 19 DRB3 alleles, 89 DRB4 alleles, 14 DRB5 alleles, 19 DQA1 alleles and 39 DQB1 alleles, with new alleles being discovered continuously. As testament to this rapid progress, a April 2007 update by the WHO nomenclature Committee for Factors of the HLA System (www.anthonynolan.com/HIG/) showed there are 545 HLA-A alleles, 895 HLA-B alleles, 307 HLA-C alleles, 8 HLA-E alleles, 12 HLA-H alleles, 9 HLA-J alleles, 6 HLA-K alleles, 4 HLA-L alleles, 4 HLA-P alleles, 3 HLA-V alleles, 3 DRA alleles, 494 DRB1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles.

All HLA-A, -B, and -C alleles have similar sequences. The same holds for DRB1, DRB3, DRB4 and DRB5 sequences. Because of these similarities, very often when a primer pair is used in the practice of polymerase chain reaction sequence-specific priming (PCR-SSP), two or more alleles will be amplified, or in a diagnostic sequence-specific oligonucleotide-probe detection (SSO) system, two or more alleles will hybridize. Therefore, for each allele to have a unique PCR-SSP or detection-SSO pattern, many pairs of primers or probes must be used. Further, the use of diagnostic hybridization SSO probes in HLA typing is confounded by the high levels of homology shared by the HLA alleles. Thus, many prior art typing methods such as those of Bugawan et al., Tissue Antigens 44:137-147 (1994), lack the accuracy desired for HLA typing and other applications.

PCR can be used to characterize the sequence on the target DNA template. If amplification occurs, the template DNA contains the same sequences as the primers used. If no amplification occurs, the sequences on the template DNA are different from the primer sequences. Newton et al., U.S. Pat. No. 5,595,890 discloses PCR diagnostic methods for typing, including molecular typing of HLA using PCR-SSP. According to this method, an unknown allele is assigned based on the pattern of positive or negative reactions from multiple rounds of PCR. The methods disclosed by Newton are limited in their effectiveness for HLA typing, however, due to the high degree of polymorphism in HLA as described above. As a consequence two primers, each with specific sequences, frequently amplify many HLA alleles, thus increasing the number of PCR amplifications required in order to assign an unknown allele. For similar reasons, multiple diagnostic probes are required for correct typing of HLA in non-PCR contexts. PCR requires a pair of primers flanking the region on the DNA template for that region to be amplified. The ability of a primer to anneal to the desired sequence depends on the length of the primer and the annealing temperature set in the PCR thermocycling program. The longer the primer, the higher the annealing temperature it needs to achieve specific amplification of a DNA sequence. PCR-SSP uses a balance between primer length and annealing temperature to achieve the specificity of the primer-directed sequence amplification.

In the clinical use of PCR-SSP systems for HLA typing, there had existed a need to use a limited number of PCR reactions to achieve as much resolution as possible whereby the number of alleles amplified by a pair of primers would be reduced (i.e., the specificity of the primers or probes would be increased). Of interest to the present invention is the disclosure of co-owned U.S. Pat. No. 6,207,379, the disclosure of which is hereby incorporated by reference, which teaches the use of diagnostic PCR primers that are characterized by non-contiguous (gap) sequences for obtaining greater discrimination between related alleles in HLA typing. In an alternative embodiment, U.S. Pat. No. 6,207,379 teaches use of diagnostic primers that hybridize to non-contiguous sequences in a target nucleic acid and amplify that target by polymerase-mediated primer extension. Despite the success of the methods of U.S. Pat. No. 6,207,379 in carrying out more specific amplification of the target HLA sequences there still remains a desire for improved methods for detection of HLA sequences in both PCR and non-PCR contexts.

The PCR invention described in U.S. Pat. No. 6,207,379 addressed the need in the art for improved methods of PCR-SSP-based molecular typing whereby the specificity of the typing can be increased so as to reduce the number of PCR reactions required for each typing. However, there still exists a need in the art for methods to probe for specific sequences in non-PCR contexts. For reasons of basic thermodynamics, probes and templates, including those with a perfect match, are in state of equilibrium between the hybridized and non-hybridized state. A probe that is at one moment attached to its target template, at another moment may not be. The polymerase in PCR plays a critical role by locking a primer in place through elongation (primer extension). In non-PCR contexts, the critical factor—the polymerase (and the subsequent elongation)—is lacking, and long-term stability of the hybridized duplex of a short probe to a target would not necessarily be expected. For these reasons it is generally considered necessary for hybridization probes to be longer than corresponding extension primers in order to assure stable duplex formation.

The U.S. Patent Publication No. US 2003-0165925 A1 incorporated by reference in its entirety, provides improved methods for detecting HLA nucleic acids and T-cell receptor nucleic acid sequences whereby the specificity of diagnostic probes is increased. The specificity is increase in these methods because at least one probe is capable of recognizing two or more regions on the target and is capable of doing so without increasing the annealing temperature of the probe to the target nucleic acid sequence. The increased specificity of the probe set reduces the number of alleles detected, thus increasing the resolution of the method, and does so at lower cost.

Currently, the methods of DNA-base tissue-typing are expensive and time consuming because these methods require detection of many different labels to distinguish different SSO probes such as by flow cytometry or visual images from a camera or microscope, such as Bioarrays. While, an unlimited number of uniquely labeled microparticles presenting different oligonucleotide probes can theoretically be prepared there exist practical limitations on the number of labels that can be distinguished and measured during a single assay using methods such as fluorescent labeled flow cytometry. Accordingly, there exists a desire in the art to maximize the number of oligonucleotide probes that can be tested in a single assay using a limited number of uniquely labeled microparticles.

SUMMARY OF INVENTION

The invention provides for methods of obtaining more data from a limited set of microparticles. The sets of microparticles currently available have a limited number of identifiable characteristics (such as fluorescent labels). There is a limited number of characteristics that can be measured at one time using conventional methods. However, the number of test molecules that need to be screened continues to increase. For example, for DNA based tissue typing, the number of HLA antigens and polymorphisms is increasing daily and a complete HLA screen of a donor sample requires hundreds of probes. Using conventional methods, a complete initial HLA screen would require multiple assays The improved methods of the invention allow for screening of more target molecules using fewer distinctly labeled microparticles and thereby measuring fewer characteristics and ultimately fewer assay runs.

The improved methods of the invention utilize a set number of microparticles that each have a different identifiable characteristic. The improvement of the invention relates to presenting one or more different probes on sets of microparticles that have the same identifiable characteristic, such as a set of microparticles each embedded with the same fluorescent label. Therefore, the assay may screen for more target molecules while detecting the same or less identifiable characteristics. For example, 100 differently labeled microparticles can be used to screen for more than 100 target molecules; or alternatively, 100 target molecules can be screened using less than 100 different labels.

The probes of the method of the invention act as binding partners for target molecules within a biological sample. The probes can be any binding partner including nucleic acids, such as oligonucleotides, primers or any nucleic acid that are complementary to target molecule nucleic acids. The binding partner may also be an antigen, such as a peptide antigen or protein, that binds to a target molecule antibody, or an antibody that binds to a peptide antigen or protein target molecule. In addition, the binding partner may be any protein that binds to a target molecule protein, such as receptors and ligands or proteins that complex. The binding interaction is the event of binding between any protein binding partners or the hybridization of a nucleic acid with a SSO probe or primer or any other complementary nucleic acid.

These methods are preferably carried out using microparticles that are presenting a probe that will bind to a target molecule within a biological sample, and this binding interaction will generate a measurable signal. According to a preferred aspect of the invention, the probe may be a sequence specific oligonucleotide (SSO) probe that will hybridize (binds) to a DNA sample. Alternatively, the probe may be a peptide, antibody or protein antigen that binds to an antibody or another protein in a biological sample.

The target molecules of the invention may be any molecule of interest in a biological sample. The methods of the invention are screening for the target molecules. In one embodiment, the methods of the invention are used to screen for tissue-typing alleles. This method can be carried out using any tissue-typing allele. The HLA tissue typing allele is described throughout the specification but these methods can be carried out using any tissue-typing antigen.

The invention provides for improved methods for tissue typing using probes conjugated to microparticles, such as microspheres or beads, having unique identifiable characteristics. The methods of the invention generate more tissue-typing information with a limited number of sets of detectably labeled and distinctly identifiable microparticles by using one or more sets of microparticles having the same detectable label but wherein the set of identically labeled microparticles comprises multiple subsets of microparticles labeled with different probes.

For example, a set may comprise 10 subsets of microparticles all labeled with the same fluorescent dye wherein the subset of microparticles has a different probe immobilized to its surface. Using this approach, an increased number of different tissue-typing antigens can be screened for using a limited number of differently labeled microparticles.

In an exemplary embodiment, the improved method of the invention may screen for 1000 different tissue-typing antigens by immobilizing 1000 different probes on a multiplicity of beads (microparticles). The labeled beads are divided into 100 sets such that each set is made up of 10 subsets of beads having 10 unique probes but which are labeled with the same fluorescent dye, or unique combination of fluorescent dyes. Accordingly, many identically labeled beads (emitting the same signals) will present a different probe. Thus, in the exemplary screen, 100 different florescent signal or combinations of signals are detected, but 1000 different probes are tested.

Conversely, many fewer unique labels can be used to screen for the same number of target molecules. Therefore, this method allows for screening of many tissue-typing antigen alleles while only using a more limited number of labeled beads. In addition, the improved methods of the invention are more efficient and require less labor. Reduced labor is required for the improved methods because there is less of a need to run a low resolution test followed by a higher resolution test.

Subsequently, a biological sample contacts the multiple sets of microparticles under conditions that promote a binding interaction such as conditions that promote antibody/antigen binding or conditions that promote nucleic acid hybridization. The binding interaction between the target molecule within the biological sample can be detected, most preferably through a signal system that generates a signal indicative of binding and detection of that signal indicates that the biological sample is positive for the target molecule.

While practice of the methods of the invention increases the number of unique target molecules assayed for by a given number of uniquely labeled beads, the methods are more susceptible to false negatives reporting contrasted with prior art methods in which all of a given bead set are specific for a particular target molecule. For example, in DNA-based HLA testing, it is frequently the case that few of the SSOs will have a hybridization partner in the DNA sample. Thus, for any given set of oligonucleotide probes as few as one subset of probes will report a positive reaction with the sample, if at all. In such a case, the remainder of subsets within a given set of probes will not report a positive reaction and the overall signal, as well as the mean and median signal, provided by all the microparticles of a given set will be low. Accordingly, there exists the possibility of a false negative being reported (i.e., a failure to report the true positive reaction). While the present invention provides for the ability to screen for a greater number of target molecules, the possibility of such false negatives can lead to devastating consequences in areas such as in the tissue transplantation art.

According to a further aspect of the present invention, the risk of false negatives is reduced by choosing a selected proportion of a set generating a positive signal for further evaluation. This step is referred to as "the filtering step'. The proportion selected is some proportion of the microparticles generating the greatest intensity of signal indicative of target molecule binding. Because some proportion of the true negatives is excluded by this method the presence of true positives can more reliably be determined.

In one embodiment, the invention provides for methods of screening for a binding interaction comprising the steps of: a) preparing multiple sets of uniquely identifiable microparticles wherein the microparticles within a set have same unique identifiable characteristic and further, wherein one or more sets comprise two or more subsets of microparticles said subset presenting at least one unique probe that acts as a binding partner for a target molecule within a biological sample, b) contacting said multiple sets of microparticles with a biological sample under conditions in which a target molecule within the biological sample binds to the probe, c) detecting the binding of a target molecule within the biological sample and the probe on said microparticles by generation of a signal indicative of the binding interaction between the target molecule and the probe, d) measuring the signal indicative of the binding interaction for said microparticles, e) determining for said set of uniquely identifiable microparticles whether the signal indicative of the binding interaction is greater than a selected threshold indicative of the presence of one or more target molecules in said biological sample; and e) determining the number of uniquely identifiable microparticle sets indicating the binding interaction.

In one aspect, the invention provides for methods wherein at least one of the subsets of microparticles within at least one of the set of uniquely identifiable microparticles are present in a fixed numerical ratio other than 1 to 1. Exemplary ratios are about 1:2, about 1 to 3, about 1 to 4, about 1 to 5, about 2 to 3, about 3 to 4, about 4 to 5, about 7 to 8, about 8 to 9, about 1 to 10, about 1 to 25, about, 1 to 50, about 1 to 100. The rations may be integral ratios or non-integral rations.

In one embodiment of the invention, the probe is a SSO probe, the target molecule is a nucleic acid, the biological sample is a sample DNA and the binding interaction is hybridization of a nucleic acid within sample DNA and the SSO probe. In one aspect of the invention, the SSO probe is specific for a tissue typing antigen allele such as HLA, HNA, blood group, KIL or TCR. The sample DNA may be obtained from any source such as from a buccal swab or blood.

In another embodiment of the invention, the probe is a peptide or protein antigen, the target molecule is an antibody and the binding interaction is binding of the antibody and the peptide or protein antigen. In one aspect of the invention, the target molecule is an antibody specific for HLA, HNA, blood group antigens, TCR or KIL.

The method of screening for a binding interaction may further comprise the steps of selecting a proportion of less than 100% of microparticles exhibiting the greatest signal indicative of the binding interaction for one or more sets of uniquely identifiable microparticles, and determining for said set(s) of uniquely identifiable microparticles whether the signal indicative of the binding interaction for the selected proportion is greater than a selected threshold indicative of the presence of one or more target molecules in said biological sample.

These methods may be carried out wherein at least two subsets of microparticles within at least one set of the uniquely identifiable microparticles are present in a fixed numerical ratio other than about 1 to 1, and wherein the ratio will determine the selected proportion of the set of microparticles. Exemplary ratios are about 1:2, about 1 to 3, about 1 to 4, about 1 to 5, about 2 to 3, about 3 to 4, about 4 to 5, about 7 to 8, about 8 to 9, about 1 to 10, about 1 to 25, about, 1 to 50, about 1 to 100. The rations may be integral ratios or non-integral ratios.

The selected proportion of a set of microparticles may be less than 50%, less than 30%, less than 20% or less than 10%. In a preferred embodiment, the selected proportion of a set of microparticles is less than or equal to the inverse of the number of subsets of microparticles presenting unique probes for said bead set.

In a further embodiment, the invention provides for methods of DNA-based tissue-typing comprising the steps of: a) preparing multiple sets of uniquely identifiable microparticles wherein the microparticles within a set have same unique identifiable characteristic and further, wherein one or more sets comprise subsets of microparticles said subset presenting at least one unique sequence specific oligonucleotide (SSO) selected to hybridize with tissue-typing antigen alleles, b) contacting said multiple sets of microparticles with a sample DNA under hybridizing conditions, c) detecting the hybridization of sample DNA and the SSOs on said microparticle by generation of a signal indicative of the hybridization of sample DNA with the SSOs, d) measuring the signal indicative of the hybridization of sample DNA and the SSOs for said microparticles, e) determining for said set of uniquely identifiable microparticles whether the signal indicative of sample DNA/SSO hybridization.

In another embodiment, the invention provides for methods of DNA-based tissue-typing comprising the steps of: a) preparing multiple sets of uniquely identifiable microparticles wherein the microparticles within a set have same unique identifiable characteristic, and further wherein said sets comprise subsets of microparticles, said subset presenting at least one unique sequence specific oligonucleotides (SSOs) selected to hybridize with tissue-typing alleles, b) contacting said multiple sets of microparticles with a sample DNA under hybridizing conditions, c) detecting the hybridization of sample DNA and the SSOs on said microparticle by generation of a signal indicative of the hybridization of sample DNA with the SSOs, d) measuring the signal indicative of the hybridization of sample DNA and the SSOs for said microparticle, e) selecting a proportion of less than 100% of microparticles exhibiting the greatest signal indicative of sample DNA/SSO hybridization for at least one set of uniquely identifiable microparticles, f) determining for said set(s) of uniquely identifiable probes whether the signal indicative of sample DNA/SSO hybridization for the selected proportion is greater than a selected threshold indicative of the presence of one or more tissue-typing antigen alleles in said sample; and g) determining the number of uniquely identifiable microparticle sets indicating DNA/SSO hybridization.

The method of DNA-tissue typing may further comprise the steps of selecting a proportion of less than 100% of microparticles exhibiting the greatest signal indicative of the DNA/SSO hybridization for at least one set of uniquely identifiable microparticles, and determining for said set(s) of uniquely identifiable microparticles whether the signal indicative of the DNA/SSO hybridization for the selected proportion is greater than a selected threshold indicative of the presence of one or more tissue-typing alleles in a biological sample.

These methods of DNA-based tissue typing may be carried out wherein at least two subsets of microparticles within at least one set of the uniquely identifiable microparticles are present in a fixed numerical ratio other than about 1 to 1. Exemplary ratios are about 1:2, about 1 to 3, about 1 to 4, about 1 to 5, about 2 to 3, about 3 to 4, about 4 to 5, about 7 to 8, about 8 to 9, about 1 to 10, about 1 to 25, about, 1 to 50, about 1 to 100. The rations may be integral ratios or non-integral rations.

The selected proportion of a set of microparticles may be less than 50%, less than 30%, less than 20% or less than 10%. In a preferred embodiment, the selected proportion of a set of microparticles is less than or equal to the inverse of the number of subsets of microparticles presenting unique SSO probes for said microparticle set.

In one aspect of the invention, the SSO probe is specific for a tissue typing antigen allele such as HLA, HNA, blood group, KIL or TCR. The sample DNA may be obtained from any source such as from a buccal swab or blood.

These methods of the invention may further comprise a step of reporting a signal for positive hybridization. The methods may also further comprise the step of selecting for each identifiable probe set a proportion of microparticles having the strongest signal.

In a further embodiment, the invention provides for methods of DNA based tissue typing comprising the step of a) contacting a multiplicity of different sets of microparticles presenting unique sequence specific oligonucleotides (SSOs) with sample DNA to identify tissue-typing antigen alleles encoded by the sample DNA, and wherein said set of microparticles is uniquely identified, and determining whether the SSO presented on said identifiable set of microparticles hybridizes with alleles within the sample DNA, b) the improvement comprising preparing multiple sets of uniquely identifiable microparticles having the same unique identifiable characteristic, wherein said set comprises subsets of microparticles each subset presenting at least one unique sequence specific oligonucleotide (SSO) selected to hybridize with HLA alleles, c) contacting said multiple sets of microparticles with a sample DNA under hybridizing conditions, d) detecting the hybridization of sample DNA and the SSOs on said microparticle by generation of a signal indicative of the hybridization of sample DNA with the SSOs, e) measuring the signal indicative of the hybridization of sample DNA and the SSOs for said microparticle, f) determining for said set of uniquely identifiable microparticles whether the signal indicative of sample DNA/SSO hybridization is greater than a selected threshold indicative of the presence of one or more HLA alleles in said sample; and g) determining the number of uniquely identifiable microparticle sets indicating DNA/SSO hybridization.

In a further embodiment, the invention provides kits for conducting a method of measuring a binding interaction comprising multiple sets of uniquely identifiable microparticles having the same unique identifiable characteristic, wherein said set comprises subsets of microparticles, said subset presenting at least one unique probe that binds to a target molecule within a biological sample. The target molecule of the kit may be HLA allele, HLA allele, HNA antigen, HNA allele blood grouping antigen, TCR or KM. In one aspect, the probe of the kit is a SSO or a primer. In another aspect, the probe of the kit is a peptide or protein antigen.

In another embodiment, the invention provides kits for conducting a method of DNA-based tissue typing comprising multiple sets of uniquely identifiable microparticles having the same unique identifiable characteristic, wherein said set comprises subsets of microparticles said subset presenting at least one unique sequence specific oligonucleotide (SSO) selected to hybridize with a tissue-typing antigen allele. The tissue-typing antigen of the kit may be s HLA, HNA, blood grouping antigen, TCR or KIL.

DETAILED DESCRIPTION

The invention is related to improved methods for tissue typing transplant donors and recipients using probes conjugated to microparticles or beads with unique identifiable characteristics. The method involves screening with a set of beads with identical identifiable characteristics, wherein different probes are immobilized on the bead. These methods include DNA-based and protein-based tissue-typing.

The method involves preparing multiple sets of beads, wherein each set has a unique identifiable characteristic. In a preferred embodiment, the unique identifiable characteristic is some combination of multiple embedded detectable label such as fluorescent dyes. Each of the beads within a set presents at least one probe that binds to a tissue-typing antigen, such as HLA in a sample DNA. For DNA-based tissue-typing the probe is a sequence specific oligonucleotide (SSO) which hybridizes to a sample DNA. For protein-based tissue typing, the probe is an peptide or protein antigen that binds to an antibody or another protein within a biological sample.

For DNA-based tissue typing, a sample DNA may be obtained from a biological sample or tissue from a transplant donor or transplant recipient, and the gene encoding the tissue-typing antigen of interest or a region containing the an allele or polymorphism of the tissue-typing antigen is amplified by PCR. The amplified sample DNA (or PCR product) contacts the multiple sets of beads under hybridizing conditions such as moderately stringent hybridization conditions or highly stringent hybridization conditions. Hybridization of the sample DNA and the SSO probe on the bead generates a signal indicative of hybridization and this signal is detected and measured with a method standard in the art such as flow cytometry or visual images generated by a microscope and/or a camera. In a preferred embodiment, the signal is generated because the sample DNA is labeled with a fluorescent dye, such as phycoerythrin (PE) or fluorescein isothiocyanate (FITC) and a label such as biotin, with the corresponding streptavidin conjugated with fluorescent dyes. The fluorescent dyes conjugated to hexahistidine also may be used in combination with sample DNA labeled with nickel. A positive event is one in which an SSO probe hybridizes to the sample DNA. The signal also may be generated using immobilized SSP primers to detect the elongation events with labeled nucleotides.

A proportion of the positive subset of beads is selected. Preferably, the selected proportion exhibits the greatest signal indicative of a specific binding interaction between the target molecule and the probe, such as sample DNA/SSO hybridization or the antibody/antigen binding, for each set of uniquely identifiable beads. The signal emitted by the selected portion of positive beads is statistically analyzed to determine the mean or median (or any other statistics such as peak, trimmed mean, trimmed peak etc.) intensity of the signal emitted by the detectable label. The portion of the subset of positive beads is preferably determined by the number of different probes and number of different labeled beads used in the screening assays. The positive beads are those that emit a signal that is greater than a selected threshold, wherein the threshold is indicative of the presence of one or more tissue-typing antigen alleles in the sample DNA. Exemplary software for analyzing the signal using a Flow cytometer is available from Luminex, Inc. (Austin, Tex.) and BD Biosciences (San Jose, Calif.). Additional software examples include WinMDI (Windows Multiple Document Interface for Flow Cytometry), FCS Express (De Novo Software, Thornhill, ON Canada), FlowJO (Tree Star, Inc.). The positive subset of beads will indicate a number of tissue-typing antigens that may be present within the sample DNA or biological sample. The data may be analyzed using software that analyzes the intensity of detectable labels, which is standard in the art.

The selected threshold to determine positive beads (after the filtering step) will be the same for any single probe. The selected threshold is commonly determined by analyzing a panel of known positive samples and a panel of known negative samples, and identifying the differential between the two. A threshold is then set within that differential.

The invention provides an improved method for DNA-based tissue typing or protein-based tissue typing, which utilizes multiple probes on beads with identical identifiable characteristics. The use of a subset of the multiple probes immobilized on beads having an identical identifiable characteristics allow for detection of a stronger signal from the positive beads since only one characteristic or signal is being detected. In addition, the signal detected using the improved method of the invention is near to the true value of the intensity of the actual signal produced by the specific hinging interaction, such as DNA/SSO hybridization or the antibody/antigen binding. The true value of intensity of the signal is that measured using the conventional methods that use beads each having a different identifiable characteristic, such each having a different fluorescent label, and a unique SSO probe or peptide probe. Thus, the signal detected using the improved method is similar to the that detected using the conventional method.

One advantage of this improved method of DNA-based tissue-typing or protein-based tissue-typing is that the initial tissue typing screen provides much information on which tissue-typing antigens are not present in the sample DNA or biological sample. Nevertheless, the information on which antigens are definitely present in the sample DNA or biological sample may be less precise because of the inherent ambiguity of the system. Methods by which the ambiguity of the system may be reduced are set out below. This approach is less expensive, because it involves fewer different identifiable beads and considerably narrows the overall potential positive antigens in a sample DNA or biological sample. Also, this approach reduces the cost of labor because fewer rounds of testing are needed. In addition, this approach allows for testing an increased number of tissue-typing antigens gene sequence because a greater number of probes may be used while reducing the number of beads used. In addition, the improved method allows for higher resolution typing in a shorter time which is advantageous because the tissue may be transplanted sooner.

Analyzing multiple subsets of microparticles within a set of microparticles having the identical identifiable characteristic may result in an increased number of false negatives. In particular, if a DNA sample only hybridizes to a few microparticles (such as one subset of microparticles) within a set, the intensity of the signal generated by the hybridization will be low and may be deemed as a negative event. i.e. false negative events To solve the problem of false negatives, a selected portion of a set generating a positive signal is chosen for further evaluation. This selected portion will be less than all (100%) of the positive set. Preferably, the selected portion of the positive set is less than 90%, less than 80%, less than 70%, less than 60%, less than 50%, less than 40%, less than 30%, less than 20% or less than 10% of the positive set of microparticles. The proportion selected may depend on the number of SSO probes and the number of total microparticles used in the tissue-typing screen. In addition, the proportion may be selected by detecting a drop off in signal, i.e. the slope of the curve for the analysis.

The inherent ambiguity of the system wherein identically labeled proteins are capable of binding with multiple different targets may be reduced by appropriate arrangement of probes in different microparticle sets and subsets. The selection of the SSO or protein-based probes on the microparticles allows for detection of particular alleles or particular antigens. For example, patterns of SSOs within a set or patterns between different sets may be designed to allow for selected elimination of certain alleles or selection of a rare alleles. Such patterns of probes may have multiple copies of the same probe within one set of microparticles or multiple copies of the same probe within different sets of microparticles. The variation in the numbers of the identical probes and the ratio of different probes allow for the generation of additional data by fewer assays.

The invention particular provides for subsets of probes within a set of microparticles, wherein the microparticles of a set have the same identifiable characteristic, and the number of probes varies between the subsets. The ratio of probes between the subsets allow for complex analysis of the presence of the target molecules, such as HLA alleles, within a biological sample. Variation of the ratios of probes between subsets within a single set of microparticles allows for a larger proportion of the positive events to be selected for further statistical analysis or stated another way, a larger portion of the events will be selected in the filtering step while reducing the potential for false negative events.

In a further embodiment, the variation in probe ratios between subsets within a single set may reduce the ambiguity within the system by allowing for identification of the target molecule based on the percentage of microparticles generating certain signals.

The use of computer algorithms will allow for the analysis of the pattern of positive probes or analysis of the variations of ratios of probes to determine specific tissue typing or to determine the presence of a rare allele verses the presence of a common allele. It is more efficient to carry out complex analyses using patterns of SSOs or differing ratios of SSOs between subsets of a set of microparticles having the same identifiable characteristic, rather than using a single set of 100 microparticles each containing a different SSO and a different identifiable characteristic.

A preferred embodiment of the invention uses microparticles presenting SSO for DNA-based tissue typing. However, the invention also provides for methods of tissue-typing using microparticles presenting a tissue-typing antigen for detection of an antibody is a biological sample. The advantages of the improved invention in view of DNA-based tissue-typing are also advantageous for protein-based assays (antigen/antibody reactions). For example, a subset of beads may be labeled with the HLA*A*0201 antigen, HLA*A*0202 antigen and/or the HLA*A*0203 antigen to detect the presence of an antibody that binds these antigens in a biological sample.

The methods of the invention may be carried out with microparticles, microbeads, beads or microsphere of any material, e.g. silica, gold, latex., polymers such as polystyrene, polysulfone and polyethyl, or hydrogel. Additional exemplary microparticles are encoded with the dyes and the oligonucleotides are immobilized to the encoded microparticles, The microparticles used in the methods of the invention are commercially available from sources such from Luminex Inc., Invitrogen (Carlsbad, Calif.), Polysciences Inc. (Warrington, Pa.) and Bangs Laboratories (Fishers, Ind.) to name a few.

The microparticles of the invention may comprise a detectable label or another identifying characteristic. The microparticles may comprise a single fluorescent dye or multiple fluorescent dyes. In one embodiment, the microparticles are internally labeled with fluorescent dyes and contain surface carboxyl groups for covalent attachment of biomolecules. In another embodiment, the microparticles are internally labeled with fluorescent dyes and contain a surface layer of Avidin for near covalent binding of biotin and biotinylated ligands. In another embodiment, the microparticles may comprise a combination of different dyes, such as a fluorescent and a non-fluorescent dye. For example, the microparticles may be labeled with E)-5-[2-(methoxycarbonyl)ethenyl]cytidine, which is a nonfluorescent molecule, that when subjected to ultraviolet (UV) irradiation yields a single product, 3-β-D-ribofuranosyl-2,7-dioxopyrido[2,3-d]pyrimidine, which displays a strong fluorescence signal. In another embodiment, the microparticles may comprise bar codes as an identifiable characteristic as described in U.S. Patent Publication No. US 20070037195.

In another embodiment, the microparticles may be nanocrystals or quantum dots. These nanocrystals are substances that absorb photons of light, then re-emit photons at a different wavelength (fluorophores). In addition, additional florescent labels, or secondary antibodies may be conjugated to the nanocrystals. These nanocrystals are commercially available form sources such as Invitrogen and Evident Technologies (Troy, N.Y.), The identifiable characteristic of the microparticle may be any nanoparticle DNA based detection methods or any nanoparticle protein based detection method. On example, is a bio bar code, which is an ultrasensitive method of detecting proteins using nanoparticle probes that are encoded with DNA that is unique to the protein target in the biological sample (Nam et al., Science 301, 1884-1886, 2003). Examples of nanoparticle DNA-based detection include colorimetric polynucleotide detection methods based on mercaptoalkyloligonucleotide-modified gold nanoparticles (Elghanian et al., Science 277, 1078-1080, 1997), chip-based detection methods that rely upon either light scattering or silver staining (Taton et al. Science 289, 1757-1760, 2000; Taton et al., J. Am. Chem. Soc., 123, 5164-5165, 2001) electrical detection method for DNA in which the target DNA is captured in the gap between two electrodes using a sandwich assay (Park et al., Science 295, 1503-1506, 2002) and DNA detection using chemoresponsive diffraction gratings interrogated simultaneously at multiple laser wavelengths (Cao et al., J. Am. Chem. Soc. 2003).

The invention can be carried out with any system that detect the identifiable characteristic or label, such as FLOW. Detection of fluorescent labels may also be carried out using a microscope or camera that will read the image on the microparticles, such as the Bioarray BeadChip (Bioarray Solutions, Ltd., Warren, N.J.). The BeadChip format combines microparticle ("bead") chemistry with semiconductor wafer processing in which binding to the microparticle is recorded using an optical microscope and camera.

The sample DNA used in the methods of the invention are isolated or extracted from a biological sample from a human transplant or transfusion donor or a human transplant or transfusion recipient. The sample DNA may be prepared using any conventional method in the art, such as those taught in Sambrook et al., Molecular Cloning: A Laboratory Manual, cold Springs Harbor Laboratories (New York, 1989). The tissue typing gene of interest, such as HLA, is amplified using PCR techniques standard in the art.

Biological samples includes whole blood, blood derivatives, red blood cell concentrates, plasma, serum, fresh frozen plasma, whole blood derived platelet concentrates, apheresis platelets, pooled platelets, intravenous gamma-globulin, cryoprecipitate, cebrospinal fluid, tissues and cells such as epithelial cells, such as those collected from the buccal cavity, stem cells, leukocytes, neutrophils and granulocytes. The biological samples may be obtained from a human donor of tissue or cells intended for transplantation or a human donor of blood or blood derivatives intended for transfusion. The biological sample may be obtained from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

SSO Probes

To carry out the methods of the invention, SSO probes are conjugated to fluorescently labeled beads. The SSO probes may also contain a label such as biotin, streptavidin, nickel, hexahistidine, digoxigenin (DIG), DNP or a fluorescent label such as FITC, PE, 6-TAMRA, CR6G, DEAC, Texas Red, Cy3, Cy3.5, CY5, Cy5.5, Cy7, Rhodamine Green X. The term "nucleotide" as used herein can refer to nucleotides present in either DNA or RNA and thus includes nucleotides that incorporate adenine, cytosine, guanine, thymine and uracil as base, the sugar moiety being deoxyribose or ribose. It will be appreciated, however, that other modified bases capable of base pairing with one of the conventional bases, adenine, cytosine, guanine, thymine and uracil, may be used in the diagnostic probe employed in the present invention. Such modified bases include, for example, 8-azaguanine and hypoxanthine. The term "oligonucleotide" as used herein refers to a molecule that is 200 nucleotides or fewer, preferred oligonucleotides are 100 nucleotides or less, 50 nucleotides or less or 25 nucleotides or less.

The term "complementary to" is used herein in relation to nucleotides to mean a nucleotide which will base pair with another specific nucleotide. Thus, adenosine monophosphate is complementary to uridine monophosphate or thymidine monophosphate and guanosine monophosphate is complementary to cytidine monophosphate. It is appreciated that while thymidine monophosphate and guanosine monophosphate may base pair under certain circumstances, they are not regarded as complementary for the purpose of this specification. It will also be appreciated that while cytosine monophosphate and adenosine monophosphate may base pair under certain circumstances, they are not regarded as complementary for the purposes of this specification. The same applies to cytosine monophosphate and uracil monophosphate.

The SSO probe used in the methods herein are selected to be "substantially" complementary to the different strands of each specific sequence to be detected. This means that the SSO probes must be sufficiently complementary to hybridize with their respective strands of sample DNA. Therefore, the SSO probe sequence need not reflect the exact sequence of the sample DNA sequence. Thus, probe sequences do not necessarily have to be exactly complementary to the target sample DNA sequences. Thus, not all probes produce a clean negative signal similar to that of a negative control for negative alleles. Depending upon the number of mismatches and what types of mismatches (G-T mismatch occasionally produces approximately the same signal as G-C match), the fluorescent signal for 1 base-pair mismatched alleles might produce a signal substantially higher than the negative control. However, as long as the signal of the true positive alleles are significantly higher than those potentially cross-reacting alleles, usually >by 10-20%, a threshold or cut-off value can be established to distinguish between positive and negative reactions.

Generally a small number of mismatches will be tolerated in the middle of the probe sequences and will allow for hybridization. In general, the degree of mismatching tolerated depends upon the SSO probe region length, which in turn affects the denaturation temperature and the annealing temperature selected of the hybridization conditions. If the denaturation temperature of the probe is close to or higher than the annealing temperature (less stringent), then the probe will still adhere to the target sequence despite a small number of (generally one or two or at most three) mismatches. A probe region may be capable of tolerating more mismatches in the middle of the sequence but its ability to do so depends on the denaturation temperature of the probe region and the annealing temperature of the selected hybridization and detection conditions.

The term "stringent" is used herein to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989).

More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

A diagnostic sequence-specific oligonucleotide-probe detection (SSO) system is a system or device that uses a diagnostic probe to assay for the presence of a particular target nucleic acid sequence. In such a system or device, the diagnostic probes may be attached to a support using linkers such as are well known in the art including the use of poly-carbon and poly-nucleotide linkers. Alternatively, target sequences can be immobilized on a solid support, such as a nitrocellulose membrane and the diagnostic probe is in solution. The diagnostic probe in the SSO includes at least one probe region. The term "probe region" refers to a nucleotide sequence on a diagnostic probe substantially complementary to a portion of the target nucleotide sequence.

Labeling can be either on the probes immobilized on the bead or on the amplified sample DNA. Direct fluorescence compounds, biotin, FITC or Digoxigenin (Dig) can be used as the tag. For the indirect detection, fluorescence or enzyme conjugated Avidine/Strepavidine (for biotin), anti-FITC antibody (for FITC), anti-Dig antibody (for Dig) will be used for detection purposes. According to one embodiment, latex beads modified with a carboxyl group can be used to immobilize probes. The carboxyl group on the beads is first activated by 1-ethyl-3-(3-dimethylaminopropyl) carbodiimide hydrochloride (EDC) and then the EDC-activated carboxyl group is reacted with the amine group at the 5' end of the oligo probes. Alternative embodiments using chemistries to link amine to amine, sulfide to amine and other chemistries may also be practiced.

Tissue-Typing Antigens

The invention provides for methods of tissue-typing screening for human leukocyte antigens (HLA). The HLA antigens are present on the cell surface of nearly every cell in the body and these antigens are in high concentrations on leukocytes.

HLA antigens are one of the major determinants the immune system uses for recognition and differentiation of self from non-self. As of April 2007, see the WHO nomenclature Committee for Factors of the HLA System (www.anthonynolan.com/HIG/), there are 545 HLA-A alleles, 895 HLA-B alleles, 307 HLA-C alleles, 8 HLA-E alleles, 12 HLA-H alleles, 9 HLA-J alleles, 6 HLA-K alleles, 4 HLA-L alleles, 4 HLA-P alleles, 3 HLA-V alleles, 3 DRA alleles, 494 DRB1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles.

The invention is not limited to methods of tissue typing comprising screening for HLA antigens. The methods of the invention can be used to screen for any antigen used for typing tissues or blood. For example, the methods can screen for killer cell immunoglobulin-like receptors (KIR), human neutrophil antigens (HNA), T Cell Receptors (TCR) and fragments thereof and blood groups, such as ABO, RH factor.

Killer Cell Immunoglobulin-like Receptors (KIRs)

Killer cell immunoglobulin-like receptors (KIRs) are members of a group of regulatory molecules found on subsets of lymphoid cells. KIR molecules have been implicated in reduced risk of relapse in patients with acute myeloid leukemia (AML) who received hematopoietic transplants that were mismatched for KIR ligands. KIR ligand incompatibility was defined as absence in recipients of donor class I allelic groups known to be ligands for inhibitory KIRs (3DL1, 2DL2/3, 2DL1 and 3DL2). Donor-versus-recipient NK cell alloreactivity is known to be capable of eliminating leukemia relapse and graft rejection, and it also protected patients against graft-versus-host-disease.

Sequence analysis of KIR cDNA has shown that most KIR genes contain variable sites, and that some are quite polymorphic. Allelic polymorphism provides additional diversity to the extent that unrelated individuals identical for both KW haplotypes are unlikely to be observed. The variation in KIR sequences can occur at positions encoding residues that affect interaction with HLA class I. Variation tends to occur throughout the gene, unlike the pattern observed in HLA class I and II genes where nucleotide variation is restricted primarily to one or two exons. KIR molecules have been implicated in reduced risk of relapse in patients with acute myeloid leukemia (AML) who received hematopoietic transplants that were mismatched for KIR ligands. KIR ligand incompatibility was defined as absence in recipients of donor class I allelic groups known to be ligands for inhibitory KIRs (3DL1, 2DL2/3, 2DL1 and 3DL2). The data indicated that donor-versus-recipient NK cell alloreactivity was capable of eliminating leukemia relapse and graft rejection, and it also protected patients against graft-versus-host-disease.

KIR genotyping can be locus or allele specific. Locus only typing detects presence or absence of each gene in a given individual, thus providing a profile of the KIR repertoire (KIR profile). The PCR sequence-specific priming (PCR-SSP) method for KIR typing has been updated to account for newly discovered loci and previously undetected alleles. A PCR sequence-specific oligonucleotide probe (PCR-SSOP) method has also been developed. Inter-laboratory collaboration has helped to authenticate the molecular genotyping assay for KIR loci (100). Over 100 different KIR genotype profiles have been found so far.

Medium- to high-resolution allele-specific reactions (PCR-SSP) have been described for 2DL1, 2DL3, 3DL1 and 3DL2 (25, 55), and a single-stranded conformational polymorphism (SSCP) assay has been used to genotype 2DL4. Development of a comprehensive assay was required for 2DL5 in order to distinguish the two highly homologous loci, 2DL5A and 2DL5B. Reverse-transcriptase PCR (RT-PCR) based on PCR-SSP is the method of choice for allotyping NK cell clones and remains largely unchanged from that described previously. Various monoclonal antibodies are available for this purpose, but specificity is limited by the high homology between KIR isotypes.

Blood Groups

Currently, there are many blood typing systems. The presence of an unfamiliar antigen on a transfused red blood cell or the presence of an antibody in donated plasma may cause a deleterious immune response which attacks the donated blood cells, causing the donated red blood cells to burst. This may also cause serious symptoms, including kidney failure and shock. Antigens also occur on other blood components, including white blood cells, platelets, and plasma proteins.

One example of current blood typing systems is the ABO system in which blood is typed based on the presence of A antigen (AA, AO), B antigen (BB or BO), both A and B antigens (AB) or the absence of both A and B (O) on the red blood cells. Additional antigen on red blood cells include MNS system (antigens M, N, S and s), the P system (antigen P1), the Lutheran system (Lu(a) and Lu(b), the Kell System (K (Kell) and k (cellano), and Kpa and Kpb), the Lewis system (Le a and Le b), the Duffy system (Fy a and Fy b) and the Kidd (JK) system (Jka and Jkb), In addition to those listed above, blood is also typed using the RH (Rhesus) system. There are three genes making up Rhesus antigens: C, D, and E, found on chromosome 1. There are two possible alleles at each locus: c or C; d or D; and e or E. One haplotype consisting of c/C, d/D, e/E is inherited from each parent, and the resulting Rhesus type of the individual depends on their inherited genotype. The haplotypes are given a code as follows: CDe is known as R1, cDE is known as R2, CDE is known as Rz, cDe is known as Ro, Cde is known r', cdE is known as R", CdE is known as Ry and cde is know as r.

Human Neutrophil Antigen

Antibodies to human neutrophil-specific antigens (HNA) were shown to cause clinical complications after transfusions such as pulmonary transfusion reactions and in some cases transfusion related acute lung injury (TRALI) or causing neonatal alloimmune neutropenia (NAIN) (Bux, et al. Transfus. Med. 2(2): 143-9, 1992). Therefore, detection of HNA specific antigen or antibodies has important clinical applications.

Human neutrophil antigens are also known as neutrophil-specific antigens or HNA. Currently there are 5 HNA antigen systems: HNA-1, HNA-2, HNA-3, HNA-4 and HNA-5. Alleles for HNA-1, 2, 4 and 5 were identified and the corresponding glycoproteins were characterized; however, the allele for HNA-3 remains unknown (reviewed by Stroncek, ASHI Quarterly 2004). There are three HNA-1 antigens (HNA-1a, HNA-1b and HNA-1c) that are expressed solely on neutrophils and are located on low affinity Fc-γ receptor IIIb. The HNA-2 system has one well established antigen (HNA-2a). HNA-2 is only expressed on neutrophils and neutrophil precursors and is located on the glycoprotein CD177 (NB1 gp). The HNA-3 system has one antigen, HNA-3a, that is also known as 5b. HNA-3 is expressed on neutrophils, lymphocytes, platelets, endothelial cells, kidney, spleen and placenta cells, and is known to be located on a 70 to 95 kD neutrophil glycoprotein. HNA-4 and HNA-5 are located on the β2 integrin. HNA-4 is expressed on granulocytes, monocytes and lymphocytes. (See Stroncek, ASHI Quarterly 2004)

T Cell Receptors

Antigenic peptides presented by the major histocompatibility complex (MHC) cell surface glycoproteins are recognized by T cells through the T cell receptor (TCR) complex, which is a multisubunit transmembrane surface complex made up of a T cell receptor and of the CD3 chains. The TCR directly binds the peptide/MHC complex, and activates the T cell through interactions with the CD3 and other components of the TCR. Therefore, TCR is involved in self and foreign tissue recognition and analyzing tissues for TCR expression may be helpful for tissue-typing transplant donors and recipients.

Kits

The invention also provides for kits to carryout the methods of the invention. In particular, the invention provides for kit for conducting a method of DNA-based tissue typing comprising a) multiple sets of microparticles having identifiable characteristics, wherein within each set every microparticles has an identical identifying characteristic and b) SSO probes, wherein a different SSO probe is immobilized to a microparticle within a set.

Other aspects and advantages of the present invention will be understood upon consideration of the following illustrative example.

EXAMPLE 1

Comparison of Conventional Method and the Method of the Invention

Bead, Probe and Sample DNA Preparation

The LABTYPE® SSO DRB1 Locus (One Lambda Inc., Canoga Park, Calif.) were used for the DNA-tissue typing analysis described below. The Luminex xMAP microsphere (Austin, Tex.) which have two fluorescent dyes embedded within. Each microsphere (or bead) had a different concentration of each of the embedded fluorescent dyes were used.

The SSO probe was labeled with amine and was conjugated to the bead. The HLA DRB1 Exon 2 was amplified from DNA isolated from a biological or tissue sample by PCR using biotinlyated primers. The resulting PCR product (denoted herein as "sample DNA") was labeled with biotin on the 5'-end The sample DNA was contacted to the bead and hybridization of the sample DNA with the SSO probe immobilized on the bead generated a fluorescent signal indicative of hybridization of the sample DNA and the SSO probe after incubating with Streptavidin conjugated with fluorescent dye phycoerythrin (PE). This fluorescent signal was detected and measured flow cytometry. (DNA can be from any source, preferably from blood or buccal swabs)

A DNA hybridization reaction between the amplified HLA gene within the sample DNA and the SSO probes immobilized on microparticles was carried out as follows. Standard gene amplification reactions containing approximately 1 ng/microliter of genomic DNA and 10 micromolar of corresponding sequence-specific biotinylated primers were set up using a pre-optimized thermocycling program. 5 microliters of resulting mixture containing amplified DRB1*0814 was denatured, neutralized and were mixed with desired probe-bound microparticles (1000 microparticles per probe per test) in 1M NaCl and 70 mM sodium phosphate buffer. The hybridization reactions were incubated at 60° C. for 15 minutes. Then the 2 volumes of 50 nM NaCl solution (pre-heated at 60° C.) was added to the mixtures, and the tubes were centrifuged for 5 minutes. Supernatant was removed without disturbing the pelleted microparticles. This washing step was repeated two more times.

The hybridized DNA was then labeled by addition of 3 volumes of 5 micrograms per microliter of phycoerythrin-streptavidin conjugate. The labeling mixture was incubated at 60° C. for five minutes and washed as described above. Washed microparticles were resuspended to 80 microliter volume with 50 nM NaCl. The hybridization signal was detected using a Luminex 100 Flow Analyzer that excites, detects and records fluorescence signal at 580 nm for individual microparticles injected into the instrument. Approximately 500 microparticles per test were analyzed to calculate trimmed mean fluorescence intensity (MFI) for each probe. Resulting MFI for each probe used in a test are then used to calculate relative hybridization signals using the MFI from appropriate positive control probes.

Positive control probes are probes that recognize a non-polymorphic region on all alleles that can be amplified by a specific primer set. The target nucleic acid strands for this invention include allelic regions that have been amplified using the polymerase chain reaction (PCR). The positive control probes are used to provide reference signal so that variation in the amount of the amplified DNA (amplicons) can be estimated. The positive control signal is used to calculate relative signal of all diagnostic probes as diagnostic probe signals are expressed as percent of positive control signal.

Conventional Analysis

For the conventional DNA-based tissue-typing method, 100 different fluorescently labeled beads were each conjugated with a different HLA specific SSO probe as described above. The beads were contacted with the sample DNA. Hybridization of the sample DNA to any of the beads was measured using a Luminex 100 Flow Analyzer.

The flow cytometry data was statistically analyzed using the Luminex 100 Flow Analyzer software. The bead of interest (Bead 37) had a trimmed mean value of fluorescent intensity of 1707. The trimmed mean is the mean calculated when a certain percentage of high and low outliers are omitted.

Analysis Using the Method of the Invention

Using the method of DNA-based tissue typing of the invention, a number of Bead 37 (750 beads) were conjugated with one of five HLA specific SSO probes that are set out in Table 1. The beads were contacted with the sample DNA. Hybridization of the sample DNA to any of the beads is measured using Luminex 100 Flow Analyzer. As 5 probes were tested, 20% of the positive bead were further analyzed.

TABLE 1

| Bead ID | Probe ID | Probe Specificity |
|---|---|---|
| 37 | OLR4916 | DRB1*0814 |
| 37 | DR245 | DRB1*0113 |
| 37 | DR250 | DRB1*1213 |
| 37 | DR260 | DRB1*0309, DRB1*0323 |
| 37 | DR228 | DRB1*0703 |

The flow cytometry data was statistically analyzed using the Luminex 100 Flow Analyzer software. This analysis included determining the size of the bead analyzed, the fluorescent intensity of each of the fluorescence dyes embedded within the bead, and a determination if the fluorescent intensities were within the desired range. The fluorescent intensities of each dye was analyzed to determine the RPI. The RPI represents the fluorescence intensity generated by the sample DNA hybridized to the bead. In this example, the RP1 represents the true fluorescence intensity of the PE labeled to the sample DNA. This value indicates that the sample DNA has hybridized to the SSO probe conjugated to Bead 37.

For Bead 37, 574 of the events had an RPI <216, and were considered negative, i.e. the sample DNA did not hybridize to the SSO probe. In addition, there were 151 positive events (RPI>5650) which indicates that the sample DNA hybridized to the SSO probe. The ratio of positive to negative events was 151:574, which is about 1:4. Therefore one out of the 5 probes were positive for the sample DNA. The mean RPI for the positive beads was 8152. This value is a stronger signal and is a enhance signal that is greater than true value that the mean RPI calculated with the conventional method (1707).

The DNA sample used in this experiment was known to be positive for only DRB1*0814 (hybridizes to probe OLR4916; see Table 1). Analysis of only 20% of the positive events indicated that Bead 37 was positive and the mean signal detected (8152) had an intensity similar to that generated by carrying out the conventional method (1 bead per 1 probe). This experiment demonstrates that the selection step of the methods of the invention enhanced a positive signal. In addition, this example demonstrates that more targets may be screened using the same number or fewer beads and the signal generated will be similar to the signal generated using the conventional method.

EXAMPLE 2

Additional Comparison of Conventional Method and the Method of the Invention An additional comparison of conventional methods of DNA based tissue-typing for HLA allelic antigens and the improved methods of the invention was carried out as described in Example 1. The sample DNA used in the methods contained amplified HLA antigen allele DRB1*0416.

The hybridization signal was detected using a Luminex 100 Flow Analyzer as described in Example 1. Resulting MFI for each probe used in a test was used to calculate relative hybridization signals using the MFI from appropriate positive control probes. Positive control probes that recognize a non-polymorphic region on all alleles that can be amplified by a specific primer set were also used.

Conventional Method

For the conventional DNA-based tissue-typing method, 100 different fluorescently labeled beads were each conjugated with a different HLA specific SSO probe as described above. The beads were contacted with the sample DNA. Hybridization of the sample DNA to any of the beads was measured using a Luminex 100 Flow Analyzer.

The flow cytometry data was statistically analyzed using the Luminex 100 Flow Analyzer software. The bead of interest (Bead 73) had a trimmed mean value of fluorescent intensity of 400.

Analysis Using the Method of the Invention

Using the method of DNA-based tissue typing of the invention, a number of Bead 73 (838 beads) were conjugated with one of five HLA specific SSO probes that are set out in Table 2. The beads were contacted with the sample DNA. Hybridization of the sample DNA to any of the beads is measured using Luminex 100 Flow Analyzer. As 5 probes were tested, 20% of the positive bead were further analyzed.

TABLE 2

| Bead ID | Probe ID | Probe Specificity |
|---|---|---|
| 73 | DR148 | DRB1*0416 |
| 73 | DR263 | DRB1*1522 |
| 73 | DR252 | DRB1*1133, DRB1*1135 DRB1*1205, DRB1*1215, |
| 73 | DR278 | DRB1*1364, DRB1*1441 |
| 73 | DR275 | DRB1*1351 |

The flow cytometry data was statistically analyzed using the Luminex 100 Flow Analyzer software as described in Example 1. For Bead 73, 672 of the events had an RPI <48 (mean=16), and were considered negative, i.e. the sample DNA did not hybridize to the SSO probe. In addition, there were 166 positive events (RPI>1457) which indicates that the sample DNA hybridized to the SSO probe. The ratio of positive to negative events was 166:672, which is about 1:4. Therefore one out of the 5 probes were positive for the sample DNA. The mean RPI for the positive beads was 2510. This value is a stronger signal and is a more true value that the mean RPI calculated with the conventional method (400).

The DNA sample used in this experiment was known to be positive for only DRB1*0416 (hybridizes to probe DR148; see Table 2). Analysis of only 20% of the positive events indicated that Bead 73 was positive and the mean signal detected (2510) had an intensity similar to that generated by carrying out the conventional method (mean is 400 for conventional method). This example substantiates the analysis described in Example 1.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A kit for conducting a method of measuring a binding interaction comprising:

multiple sets of microparticles, the microparticles of each set having an identifiable characteristic unique to each set such that each set is distinguishable from the other sets, wherein each set comprises at least two subsets of microparticles presenting a probe unique to each subset, wherein the probe of each subset binds to a different target molecule within a biological sample from the target molecule bound by other subsets, forming a binding complex with the target molecule; and a labeling reagent for labeling the binding complex with a detectable label that produces a measurable signal when a specific binding complex is present, and wherein the signal varies in intensity such that only the microparticles exhibiting greatest signal intensity, which comprises a proportion of less than 100% of the microparticles, are selected for analysis.

2. The kit of claim 1, wherein the target molecule is selected from the group consisting of a human leukocyte antigen (HLA), a HLA allele, a human neutrophil antigen (HNA), a HNA allele, a blood grouping antigen, a T cell receptor (TCR) and a killer cell immunoglobulin-like receptor (KIR).

3. The kit of claim 1, wherein the probe is a sequence specific oligonucleotide or primer.

4. The kit of claim 1, wherein the probe is a peptide or protein antigen.

5. The kit of claim 1, wherein the target molecule that binds to the probe is an antibody.

6. The kit of claim 1, wherein a set of uniquely identifiable microparticles comprises at least two of the subsets of microparticles which are present in a fixed numerical ratio other than about 1 to 1.

7. A kit for identifying tissue typing antigen alleles from a biological sample, the kit comprising:

multiple sets of microparticles, the microparticles of each set having an identifiable characteristic unique to each set such that each set is distinguishable from the other sets, wherein each set comprises at least two subsets of microparticles presenting a sequence specific oligonucleotide (SSO) or primer unique to each subset, wherein the SSO or primer of each subset comprises a sequence selected to hybridize with a different tissue-typing antigen allele which may be present in the sample to form one or more hybridization products, and a labeling reagent for labeling the one or more hybridization products with a detectable label that produces a measurable signal when a specific hybridization product is present, and wherein the signal varies in intensity such that only the microparticles exhibiting greatest signal intensity, which comprises a proportion of less than 100% of the microparticles, are selected for analysis.

8. The kit of claim 7, wherein the tissue-typing antigen allele is selected from the group consisting of a human leukocyte antigen (HLA), a human neutrophil antigen (HNA), a blood grouping antigen, a T cell receptor (TCR) and a killer cell immunoglobulin-like receptor (KIR) antigen.

9. The kit of claim 7, wherein a set of uniquely identifiable microparticles comprises at least two of the subsets of microparticles which are present in a fixed numerical ratio other than about 1 to 1.

10. A kit for identifying human leukocyte antigen (HLA) alleles from a biological sample, the kit comprising:

multiple sets of microparticles, the microparticles of each set having an identifiable characteristic unique to each set, wherein each set comprises at least two subsets of microparticles presenting a sequence specific oligonucleotide (SSO) unique to each subset, wherein the SSO of each subset comprises a sequence selected to hybridize with a different HLA allele which may be present in the sample to form one or more hybridization products, and a labeling reagent for labeling the one or more hybridization products with a detectable label that produces a measurable signal when a specific hybridization product is present, and wherein the signal varies in intensity such that only the microparticles exhibiting greatest signal intensity, which comprises a proportion of less than 100% of the microparticles, are selected for analysis.

11. The kit of claim 10, wherein a set of uniquely identifiable microparticles comprises at least two of the subsets of microparticles which are present in a fixed numerical ratio other than about 1 to 1.

* * * * *

UNITED STATES PATENT AND TRADEMARK OFFICE

CERTIFICATE OF CORRECTION

PATENT NO. : 9,556,483 B2
APPLICATION NO. : 14/293609
DATED : January 31, 2017
INVENTOR(S) : Jar-How Lee et al.

It is certified that error appears in the above-identified patent and that said Letters Patent is hereby corrected as shown below:

On the Title Page

At item (71), Line 1, "One Lambda" should be -- One Lambda, Inc. --.

At item (72), Line 1, "Angelos," should be -- Angeles, --.

At item (73), Line 1, "INC." should be -- INC., Canoga Park, CA (US) --.

At item (74), Line 1, "Marshall" should be -- Marshall, --.

At item (57), Line 4, "one of more" should be -- one or more --.

Signed and Sealed this
Nineteenth Day of September, 2017

Joseph Matal

Joseph Matal
*Performing the Functions and Duties of the*
*Under Secretary of Commerce for Intellectual Property and*
*Director of the United States Patent and Trademark Office*